(12) United States Patent
Misener et al.

(10) Patent No.: US 12,181,720 B2
(45) Date of Patent: Dec. 31, 2024

(54) DISINFECTING COVERS FOR FUNCTIONAL CONNECTORS OF MEDICAL DEVICES AND METHODS THEREOF

(71) Applicant: Bard Access Systems, Inc., Salt Lake City, UT (US)

(72) Inventors: Anthony K. Misener, Bountiful, UT (US); Steffan Sowards, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/524,620

(22) Filed: Nov. 30, 2023

(65) Prior Publication Data

US 2024/0094475 A1    Mar. 21, 2024

Related U.S. Application Data

(63) Continuation of application No. 17/499,644, filed on Oct. 12, 2021, now Pat. No. 11,899,249.
(Continued)

(51) Int. Cl.
  *G02B 6/38*  (2006.01)
  *A61B 46/00*  (2016.01)
  (Continued)

(52) U.S. Cl.
  CPC ......... *G02B 6/3866* (2013.01); *G02B 6/3849* (2013.01); *A61B 46/10* (2016.02);
  (Continued)

(58) Field of Classification Search
  None
  See application file for complete search history.

(56) References Cited

U.S. PATENT DOCUMENTS

| | | |
|---|---|---|
| 3,493,288 A | 2/1970 | Oltman et al. |
| 4,813,429 A | 3/1989 | Eshel et al. |
| | (Continued) | |

FOREIGN PATENT DOCUMENTS

| | | |
|---|---|---|
| CA | 3025240 A1 | 11/2017 |
| DE | 102016109601 A1 | 11/2017 |
| | (Continued) | |

OTHER PUBLICATIONS

U.S. Appl. No. 17/187,536, filed Feb. 26, 2021 Non-Final Office Action dated Dec. 15, 2023.
(Continued)

*Primary Examiner* — Jerry Rahll
(74) *Attorney, Agent, or Firm* — Rutan & Tucker LLP

(57) ABSTRACT

Disclosed are disinfecting covers for optical-fiber connectors. For example, a male disinfecting cover can include a plug, a bore of the plug, an absorbent disposed in the bore, and a disinfectant absorbed by the absorbent. The plug is configured to insert into a receptacle of a female optical-fiber connector. A female disinfecting cover can include a body, a receptacle in the body, an absorbent disposed in the receptacle, and a disinfectant absorbed by the absorbent. The receptacle is configured to accept a male optical-fiber connector. Whether the disinfecting cover is male or female, the absorbent is configured to contact the ferrule and the optical fiber disposed of the optical-fiber connector. Methods can include at least a method of using the male or female disinfecting cover.

16 Claims, 4 Drawing Sheets

Related U.S. Application Data

(60) Provisional application No. 63/091,165, filed on Oct. 13, 2020.

(51) Int. Cl.
  *A61B 46/10* (2016.01)
  *A61B 90/30* (2016.01)
  *A61L 15/28* (2006.01)
  *A61L 15/42* (2006.01)

(52) U.S. Cl.
  CPC ............... *A61B 46/40* (2016.02); *A61B 90/30* (2016.02); *A61B 2090/306* (2016.02); *A61L 15/28* (2013.01); *A61L 15/425* (2013.01)

(56) References Cited

U.S. PATENT DOCUMENTS

| | | | |
|---|---|---|---|
| 5,099,845 A | 3/1992 | Besz et al. | |
| 5,163,935 A | 11/1992 | Black et al. | |
| 5,178,153 A | 1/1993 | Einzig | |
| 5,207,672 A | 5/1993 | Roth et al. | |
| 5,211,165 A | 5/1993 | Dumoulin et al. | |
| 5,220,703 A * | 6/1993 | Kanayama | B08B 11/00 15/210.1 |
| 5,275,151 A | 1/1994 | Shockey et al. | |
| 5,423,321 A | 6/1995 | Fontenot | |
| 5,454,807 A | 10/1995 | Lennox et al. | |
| 5,517,997 A | 5/1996 | Fontenot | |
| 5,599,492 A | 2/1997 | Engelson | |
| 5,622,170 A | 4/1997 | Schulz | |
| 5,633,494 A | 5/1997 | Danisch | |
| 5,693,043 A | 12/1997 | Kittrell et al. | |
| 5,740,808 A | 4/1998 | Panescu et al. | |
| 5,827,313 A | 10/1998 | Ream | |
| 5,872,879 A | 2/1999 | Hamm | |
| 5,873,842 A | 2/1999 | Brennen et al. | |
| 5,879,306 A | 3/1999 | Fontenot et al. | |
| 5,906,579 A | 5/1999 | Vander Salm et al. | |
| 6,069,698 A | 5/2000 | Ozawa et al. | |
| 6,081,741 A | 6/2000 | Hollis | |
| 6,178,346 B1 | 1/2001 | Amundson et al. | |
| 6,208,887 B1 | 3/2001 | Clarke | |
| 6,210,362 B1 | 4/2001 | Ponzi | |
| 6,319,227 B1 | 11/2001 | Mansouri-Ruiz | |
| 6,343,227 B1 | 1/2002 | Crowley | |
| 6,398,721 B1 | 6/2002 | Nakamura et al. | |
| 6,485,482 B1 | 11/2002 | Belef | |
| 6,564,089 B2 | 5/2003 | Izatt et al. | |
| 6,593,884 B1 | 7/2003 | Gilboa et al. | |
| 6,597,941 B2 | 7/2003 | Fontenot et al. | |
| 6,619,857 B2 * | 9/2003 | Miyake | G02B 6/3866 15/210.1 |
| 6,650,923 B1 | 11/2003 | Lesh et al. | |
| 6,685,666 B1 | 2/2004 | Fontenot | |
| 6,687,010 B1 | 2/2004 | Horii et al. | |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 6,975,803 B2 * | 12/2005 | Koide | G02B 6/3807 385/134 |
| 7,132,645 B2 | 11/2006 | Korn | |
| 7,273,056 B2 | 9/2007 | Wilson et al. | |
| 7,344,533 B2 | 3/2008 | Pearson et al. | |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 | 10/2009 | Casscells, III et al. | |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 | 8/2011 | Wilson et al. | |
| 8,032,200 B2 | 10/2011 | Tearney et al. | |
| 8,054,469 B2 | 11/2011 | Nakabayashi et al. | |
| 8,060,187 B2 | 11/2011 | Marshik-Geurts et al. | |
| 8,073,517 B1 | 12/2011 | Burchman | |
| 8,078,261 B2 | 12/2011 | Imam | |
| 8,187,189 B2 | 5/2012 | Jung et al. | |
| 8,197,494 B2 | 6/2012 | Jaggi et al. | |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 | 12/2013 | Snow et al. | |
| 8,700,358 B1 | 4/2014 | Parker, Jr. | |
| 8,781,555 B2 | 7/2014 | Burnside et al. | |
| 8,798,721 B2 | 8/2014 | Dib | |
| 8,968,331 B1 | 3/2015 | Sochor | |
| 8,979,871 B2 | 3/2015 | Tyc et al. | |
| 9,119,551 B2 | 9/2015 | Qi et al. | |
| 9,186,046 B2 | 11/2015 | Ramamurthy et al. | |
| 9,339,206 B2 | 5/2016 | Grunwald | |
| 9,345,510 B2 | 5/2016 | Patel et al. | |
| 9,360,630 B2 | 6/2016 | Jenner et al. | |
| 9,560,954 B2 | 2/2017 | Jacobs et al. | |
| 9,572,492 B2 | 2/2017 | Simpson et al. | |
| 9,622,706 B2 | 4/2017 | Dick et al. | |
| 9,645,326 B1 * | 5/2017 | Sausse | G02B 6/3849 |
| 9,649,048 B2 | 5/2017 | Cox et al. | |
| 9,678,275 B1 | 6/2017 | Griffin | |
| 9,678,284 B2 | 6/2017 | Coggi et al. | |
| 10,231,643 B2 | 3/2019 | Grunwald | |
| 10,231,753 B2 | 3/2019 | Burnside et al. | |
| 10,258,240 B1 | 4/2019 | Eberle et al. | |
| 10,327,830 B2 | 6/2019 | Grant et al. | |
| 10,349,890 B2 | 7/2019 | Misener et al. | |
| 10,448,837 B2 | 10/2019 | Manzke et al. | |
| 10,492,876 B2 | 12/2019 | Anastassiou et al. | |
| 10,568,586 B2 | 2/2020 | Begin et al. | |
| 10,620,386 B2 | 4/2020 | Van Der Mark et al. | |
| 10,631,718 B2 | 4/2020 | Petroff et al. | |
| 10,932,670 B2 | 3/2021 | Smith et al. | |
| 10,939,889 B2 | 3/2021 | Flexman et al. | |
| 10,992,078 B2 | 4/2021 | Thompson et al. | |
| 10,992,079 B2 | 4/2021 | Stats et al. | |
| 11,000,207 B2 | 5/2021 | Burnside et al. | |
| 11,000,265 B1 | 5/2021 | Ryu et al. | |
| 11,123,047 B2 | 9/2021 | Jaffer et al. | |
| 11,284,916 B2 | 3/2022 | Patel et al. | |
| 11,382,653 B2 | 7/2022 | Patel et al. | |
| 11,525,670 B2 | 12/2022 | Messerly et al. | |
| 11,850,073 B2 | 12/2023 | Wright et al. | |
| 11,931,112 B2 | 3/2024 | Thompson et al. | |
| 2002/0019627 A1 | 2/2002 | Maguire et al. | |
| 2002/0166190 A1 * | 11/2002 | Miyake | G02B 6/3866 15/210.1 |
| 2002/0198457 A1 | 12/2002 | Tearney et al. | |
| 2003/0045798 A1 | 3/2003 | Hular et al. | |
| 2003/0092995 A1 | 5/2003 | Thompson | |
| 2004/0111020 A1 | 6/2004 | Long | |
| 2004/0111147 A1 | 6/2004 | Rabkin et al. | |
| 2004/0242995 A1 | 12/2004 | Maschke | |
| 2004/0260182 A1 | 12/2004 | Zuluaga et al. | |
| 2005/0033264 A1 | 2/2005 | Redinger | |
| 2006/0013523 A1 | 1/2006 | Childlers et al. | |
| 2006/0036164 A1 | 2/2006 | Wilson et al. | |
| 2006/0100610 A1 | 5/2006 | Wallace et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0060847 A1 | 3/2007 | Leo et al. | |
| 2007/0156019 A1 | 7/2007 | Larkin et al. | |
| 2007/0179485 A1 | 8/2007 | Yeik et al. | |
| 2007/0201793 A1 | 8/2007 | Askins et al. | |
| 2007/0287886 A1 | 12/2007 | Saadat | |

(56) References Cited

U.S. PATENT DOCUMENTS

| | | |
|---|---|---|
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2014/0378945 A1 | 12/2014 | Beri |
| 2015/0029511 A1 | 1/2015 | 'T Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0301288 A1* | 10/2015 | Thornton, Jr. ........ G02B 6/3825 385/76 |
| 2015/0320977 A1 | 11/2015 | Vitullo et al. |
| 2016/0018602 A1 | 1/2016 | Govari et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2017/0017048 A1 | 1/2017 | Coggi et al. |
| 2017/0020394 A1 | 1/2017 | Harrington |
| 2017/0052091 A1 | 2/2017 | Mori |
| 2017/0082806 A1* | 3/2017 | Van Der Mark ...... G02B 6/387 |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2018/0067268 A1* | 3/2018 | Murakami ................ B08B 1/30 |
| 2018/0095231 A1 | 4/2018 | Lowell et al. |
| 2018/0113038 A1 | 4/2018 | Janabi-Sharifi et al. |
| 2018/0140170 A1 | 5/2018 | Van Putten et al. |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1 | 12/2018 | Zaborsky |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0188036 A1 | 6/2020 | Ding et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1* | 9/2021 | Rohr Daniel ............. B08B 1/32 |
| 2021/0282867 A1 | 9/2021 | Tegg et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |

(56) References Cited

U.S. PATENT DOCUMENTS

| | | |
|---|---|---|
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0180470 A1 | 6/2024 | Sowards et al. |
| 2024/0215917 A1 | 7/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 9964099 A1 | 12/1999 |
| WO | 2006080076 A1 | 8/2006 |
| WO | 2006122001 A2 | 11/2006 |
| WO | 2009155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016061431 A1 | 4/2016 |
| WO | 2016193051 A1 | 12/2016 |
| WO | 2018071490 A1 | 4/2018 |
| WO | 2018096491 A1 | 5/2018 |
| WO | 2019037071 A1 | 2/2019 |
| WO | 2019046769 A1 | 3/2019 |
| WO | 2019230713 A1 | 12/2019 |
| WO | 2020142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022031613 A1 | 2/2022 |
| WO | 2022081586 A1 | 4/2022 |
| WO | 2022081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

U.S. Appl. No. 17/535,406, filed Nov. 24, 2021 Non-Final Office Action dated Feb. 15, 2024.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2021/059755 filed Nov. 17, 2021 International Search Report and Written Opinion dated Apr. 29, 2022.
PCT/US2021/060849 filed Nov. 24, 2021 International Search Report and Written Opinion dated Mar. 9, 2022.
PCT/US2022/024934 filed Apr. 14, 2022 International Search Report and Written Opinion dated Jul. 18, 2022.
PCT/US2022/043698 filed Sep. 15, 2022 International Search Report and Written Opinion dated Dec. 19, 2022.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020042 filed Apr. 26, 2023 International Search Report and Written Opinion dated Sep. 26, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/185,777, filed Feb. 25, 2021 Non-Final Office Action dated Feb. 9, 2022.
U.S. Appl. No. 17/185,777, filed Feb. 25, 2021 Notice of Allowance dated Jun. 10, 2022.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/187,536, filed Feb. 26, 2021 Non-Final Office Action dated May 17, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Non Final Office Action dated Jun. 7, 2023.
U.S. Appl. No. 17/217,852, filed Mar. 30, 2021 Notice of Allowance dated Nov. 7, 2023.
U.S. Appl. No. 17/217,852, filed Mar. 30, 2021 Restriction Requirement dated Mar. 21, 2023.
U.S. Appl. No. 17/499,644, filed Oct. 12, 2021 Notice of Allowance dated Sep. 18, 2023.
U.S. Appl. No. 17/499,644, filed Oct. 12, 2021 Restriction Requirement dated Jul. 11, 2023.
U.S. Appl. No. 17/535,406, filed Nov. 24, 2021 Restriction Requirement dated Nov. 24, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
U.S. Appl. No. 17/967,794, filed Oct. 17, 2022 Notice of Allowance dated Feb. 15, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide- coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.

(56) References Cited

OTHER PUBLICATIONS

PCT/US2023/082605 filed Dec. 5, 2023 International Search Report and Written Opinion dated Feb. 28, 2024.
U.S. Appl. No. 17/187,536, filed Feb. 26, 2021 Final Office Action dated Jul. 2, 2024.
U.S. Appl. No. 17/191,551, filed Mar. 3, 2021 Non-Final Office Action dated Aug. 16, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/689,773, filed Mar. 8, 2022 Non-Final Office Action dated Mar. 19, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 17/731,155 filed Apr. 27, 2022 Non-Final Office Action dated Aug. 22, 2024.
U.S. Appl. No. 17/849,447, filed Jun. 24, 2022 Final Office Action dated Aug. 8, 2024.
U.S. Appl. No. 17/849,447, filed Jun. 24, 2022 Non-Final Office Action dated Apr. 10, 2024.

\* cited by examiner

DISINFECTING COVERS FOR FUNCTIONAL CONNECTORS OF MEDICAL DEVICES AND METHODS THEREOF

PRIORITY

This application is a division of U.S. patent application Ser. No. 17/499,644, filed Oct. 12, 2021, now U.S. Pat. No. 11,899,249, which claims the benefit of priority to U.S. Provisional Application No. 63/091,165, filed Oct. 13, 2020, each of which is incorporated by reference in its entirety into this application.

BACKGROUND

Some multiple-use medical devices are used in relatively close proximity to patients so that the multiple-use medical devices can be functionally connected to single-use medical devices by functional connectors thereof. Being in close proximity to the patients, there are risks of contaminating the multiple-use medical devices with, for example, bodily fluids or bodily fluid-borne pathogens, as well as spreading such contamination to subsequent patients or other clinical areas in which the multiple-use medical devices are used. What is needed are disinfecting covers for functional connectors of the multiple-use medical devices that disinfect the functional connectors between uses.

Disclosed herein are disinfecting covers for functional connectors of medical devices and methods thereof that address the foregoing.

SUMMARY

Disclosed herein is a disinfecting cover for an optical-fiber connector including, in some embodiments, a plug, a bore of the plug, an absorbent disposed in the bore, and a disinfectant absorbed by the absorbent. The plug is configured to insert into a receptacle of the optical-fiber connector. The absorbent is configured to contact a ferrule of the optical-fiber connector. The ferrule has an optical fiber disposed therein. The disinfectant is configured to disinfect at least the ferrule and the optical fiber.

In some embodiments, the disinfecting cover further includes one or more interlocking features. The one-or-more interlocking features are configured to interlock with the optical-fiber connector and maintain the plug in the receptacle of the optical-fiber connector when the disinfecting cover is inserted in the optical-fiber connector.

In some embodiments, the disinfecting cover further includes a handle opposite the plug. The handle is configured to enable a person to insert the plug into the receptacle of the optical-fiber connector or remove the plug from the receptacle of the optical-fiber connector by way of the handle.

In some embodiments, the plug and handle are integrally molded from a thermoplastic. The thermoplastic is selected from acrylonitrile butadiene styrene, polyethylene, polycarbonate, polyamide, high-impact polystyrene, and polypropylene.

In some embodiments, the absorbent is a compressible sponge of polyester, polyurethane, or cellulose.

In some embodiments, the sponge is configured to release a portion of the disinfectant absorbed thereby when compressed into the bore of the plug by the ferrule of the optical-fiber connector.

In some embodiments, the disinfectant is an aqueous solution of isopropanol.

In some embodiments, the solution is at least 70% isopropanol by volume.

In some embodiments, the disinfecting cover further includes a communication module. The communication module is configured to communicate with a medical device including the optical-fiber connector and indicate to the medical device when the optical-fiber connector is covered by the disinfecting cover.

In some embodiments, a cleaning cycle including cleaning or drying is initiated upon the communication module indicating to the medical device the optical-fiber connector is covered by the disinfecting cover.

In some embodiments, actuation of a cleaning action is initiated upon the communication module indicating to the medical device the optical-fiber connector is covered by the disinfecting cover.

In some embodiments, the disinfecting cover is integrated into a portal in a procedural barrier for a medical procedure. The portal is configured to enable functional connections between medical devices on opposing sides of the procedural barrier.

Also disclosed herein is a disinfecting cover for an optical-fiber connector including, in some embodiments, a body, a receptacle in the body, an absorbent disposed in the receptacle, and a disinfectant absorbed by the absorbent. The receptacle is configured to accept the optical-fiber connector therein. The absorbent is configured to contact a ferrule of the optical-fiber connector. The ferrule has an optical fiber disposed therein. The disinfectant is configured to disinfect at least the ferrule and the optical fiber.

In some embodiments, the disinfecting cover further includes one or more interlocking features. The one-or-more interlocking features are configured to interlock with the optical-fiber connector and maintain the optical-fiber connector in the receptacle of the body when the optical-fiber connector is inserted in the disinfecting cover.

In some embodiments, the disinfecting cover further includes a handle incorporated into the body or extending therefrom. The handle is configured to enable a person to insert the optical-fiber connector into the receptacle of the body or remove the optical-fiber connector from the receptacle when holding the disinfecting cover by the handle.

In some embodiments, the body and handle are integrally molded from a thermoplastic. The thermoplastic is selected from acrylonitrile butadiene styrene, polyethylene, polycarbonate, polyimide, high-impact polystyrene, and polypropylene.

In some embodiments, the absorbent is a compressible sponge of polyester, polyurethane, or cellulose.

In some embodiments, the sponge is configured to release a portion of the disinfectant absorbed thereby when compressed into the receptacle of the body by the ferrule of the optical-fiber connector.

In some embodiments, the disinfectant is an aqueous solution of isopropanol.

In some embodiments, the solution is at least 70% isopropanol by volume.

In some embodiments, the disinfecting cover further includes a communication module. The communication module is configured to communicate with a medical device including the optical-fiber connector and indicate to the medical device when the optical-fiber connector is covered by the disinfecting cover.

In some embodiments, a cleaning cycle including cleaning or drying is initiated upon the communication module indicating to the medical device the optical-fiber connector is covered by the disinfecting cover.

In some embodiments, actuation of a cleaning action is initiated upon the communication module indicating to the medical device the optical-fiber connector is covered by the disinfecting cover.

In some embodiments, the disinfecting cover is integrated into a portal in a procedural barrier for a medical procedure. The portal is configured to enable functional connections between medical devices on opposing sides of the procedural barrier.

Also disclosed herein is a method for disinfecting optical-fiber connectors. The method includes, in some embodiments, a disconnecting step, a first inserting step, a second inserting step, and a storing step. The disconnecting step includes disconnecting a male optical-fiber connector from a female optical-fiber connector. The first inserting step includes inserting the male optical-fiber connector into a female disinfecting cover, thereby disinfecting at least a ferrule and an optical fiber of the male optical-fiber connector. The second inserting step includes inserting a male disinfecting cover into a female optical-fiber connector, thereby disinfecting at least a ferrule and an optical fiber of the female optical-fiber connector. The storing step includes keeping the male optical-fiber connector or the female optical-fiber connector in its respective disinfecting cover until connecting the male optical-fiber connector or the female optical-fiber connector to each other or another complementary optical-fiber connector.

In some embodiments, the first inserting step includes inserting the male optical-fiber connector into a receptacle of a body of the female disinfecting cover. The receptacle includes an absorbent having a disinfectant absorbed by the absorbent.

In some embodiments, the first inserting step includes compressing the absorbent into the receptacle, thereby releasing a portion of the disinfectant for the disinfecting of the male optical-fiber connector.

In some embodiments, the second inserting step includes inserting a plug of the disinfecting cover into a receptacle of the female optical-fiber connector. The plug includes a bore with an absorbent having a disinfectant absorbed by the absorbent.

In some embodiments, the second inserting step includes compressing the absorbent into the bore, thereby releasing a portion of the disinfectant for the disinfecting of the female optical-fiber connector.

In some embodiments, the method mitigates contamination of multiple-use medical devices between uses with different patients.

These and other features of the concepts provided herein will become more apparent to those of skill in the art in view of the accompanying drawings and following description, which describe particular embodiments of such concepts in greater detail.

DESCRIPTION

Figure 1:
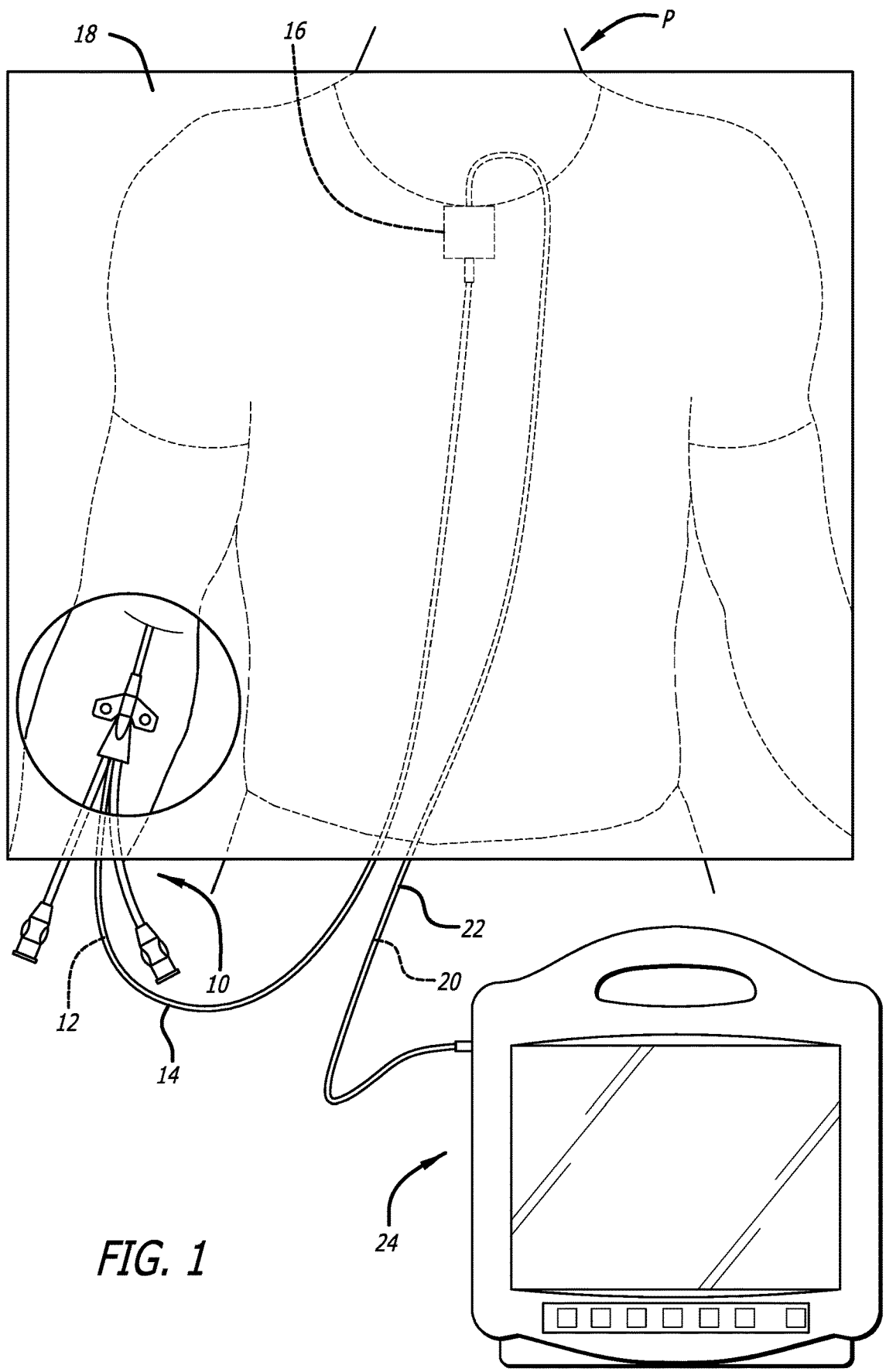
FIG. 1 illustrates functionally connected single-use and multiple-use medical devices of an optical shape-sensing system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Figure 2:
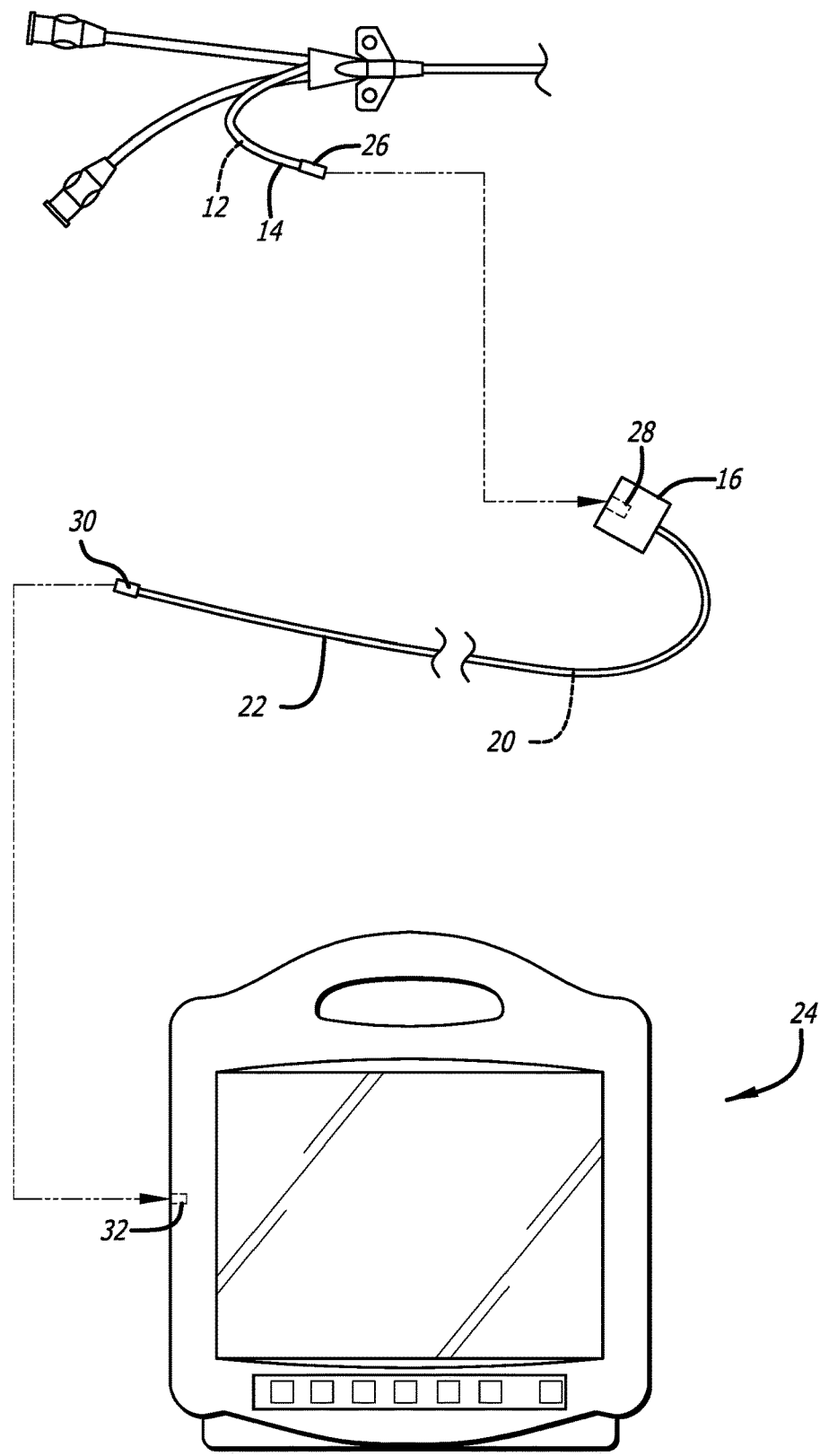
FIG. 2 illustrates functional connectors of the multiple-use medical devices of FIG. 1 in accordance with some embodiments.

As set forth above, some multiple-use medical devices are used in relatively close proximity to patients so that the multiple-use medical devices can be functionally connected to single-use medical devices by functional connectors thereof. For example, FIG. 1 illustrates an optical shape-sensing system including a single-use peripherally inserted central catheter ("PICC") 10 having an optical-fiber stylet 12 disposed in an extension tube 14 functionally connected to a relay module 16 over a patient P but under a sterile drape 18. The relay module 16, in turn, includes an optical fiber 20 disposed in a patch cable 22 functionally connected to a console 24 or an optical interrogator thereof. FIG. 2 illustrates functional connectors of the foregoing single-use and multiple-use medical devices including a male optical-fiber connector 26 of the PICC 10, a female optical-fiber connector 28 of the relay module 16, a male optical-fiber connector 30 of the patch cable 22, and the female optical-fiber connector 32 of the console 24 or the optical interrogator thereof. With the multiple-use medical devices such as the relay module 16, the patch cable 22, and the console 24 being in close proximity to the patients, there are risks of contaminating the multiple-use medical devices with, for example, bodily fluids or bodily fluid-borne pathogens, as well as spreading such contamination to subsequent patients or other clinical areas in which the multiple-use medical devices are used. Again, disinfecting covers for functional connectors of the multiple-use medical devices that disinfect the functional connectors between uses are needed.

Disclosed herein are disinfecting covers for functional connectors of medical devices and methods thereof. While the disinfecting covers and the methods thereof are primarily described for optical shape-sensing systems, the disinfecting covers and the methods thereof are not limited thereto. Indeed, some medical devices include electrical connectors instead of optical connectors or in addition to optical connectors. Whether the functional connectors are optical connectors, electrical connectors, or a combination thereof, the need for the disinfecting covers for the functional connectors and methods thereof remains. Thus, it should be understood the concepts provided herein for optical-fiber connectors can be extended to electrical connectors or combinations thereof to the same effect as set forth herein for the optical-fiber connectors.

Disinfecting Covers

Figure 3:
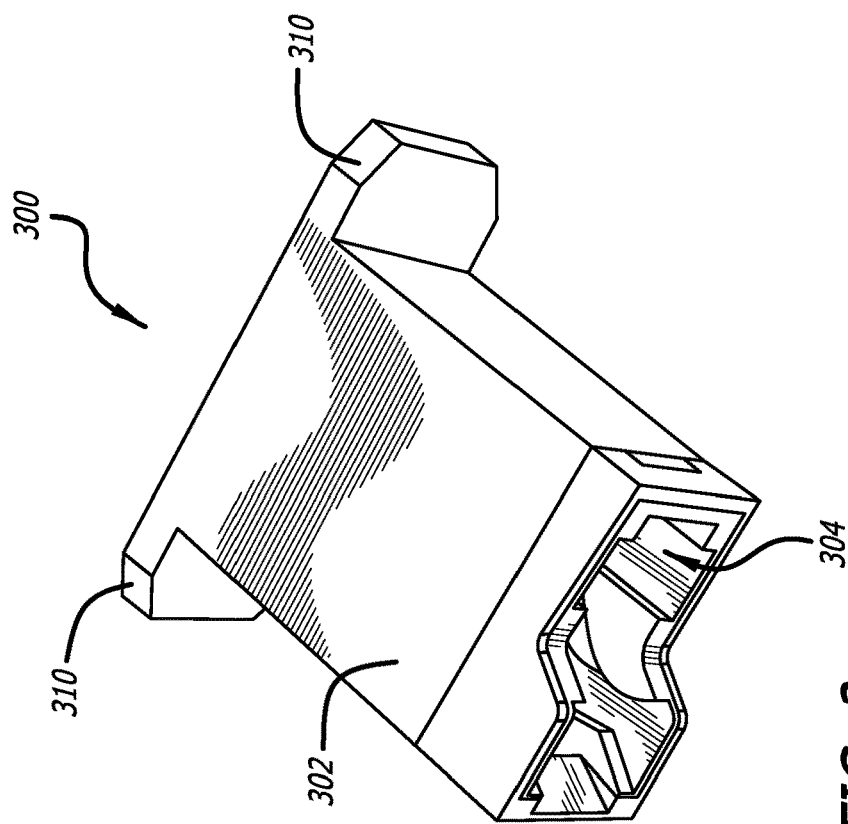
FIG. 3 illustrates a female disinfecting cover for a male optical-fiber connector in accordance with some embodiments.
Figure 5:
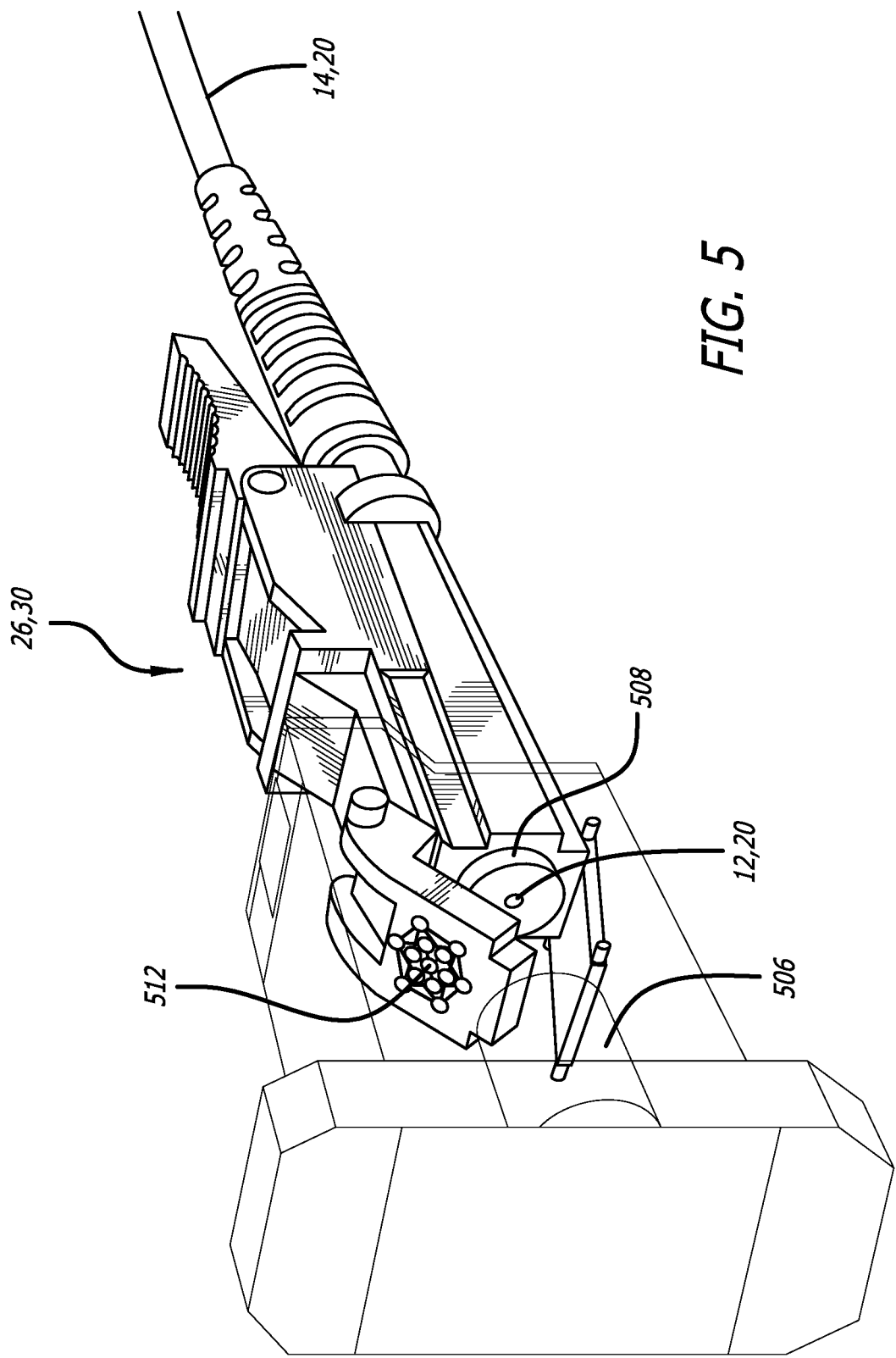
FIG. 5 illustrates inserting a male optical-fiber connector into the female disinfecting cover in accordance with some embodiments.

FIG. 3 illustrates a female disinfecting cover 300 for a male optical-fiber connector in accordance with some embodiments. FIG. 5 illustrates inserting a male optical-fiber connector into the female disinfecting cover 300 in accordance with some embodiments.

As shown, the female disinfecting cover 300 is configured to accept a male optical-fiber connector such as the male optical-fiber connector 26 or 30 inserted therein for disinfecting the male optical-fiber connector 26 or 30, as well as protecting the male optical-fiber connector 26 or 30 from dust.

The female disinfecting cover 300 includes a body 302, a receptacle 304 in the body 302, an absorbent 506 disposed in the receptacle 304, and a disinfectant absorbed by the absorbent 506. As shown, the female disinfecting cover 300 can further include a handle 310, as well as one or more interlocking features generally shown. While there are many different male optical-fiber connectors, the male optical-fiber connector 26 or 30 is representative in that it includes a ferrule 508 having the optical fiber 12 or 20 disposed therein. The absorbent 560 is configured to contact the ferrule 508 and the optical fiber 12 or 20 disposed therein when the male optical-fiber connector 26 or 30 is inserted into the female disinfecting cover 300. The disinfectant is configured to disinfect at least the ferrule 508 and the optical fiber 12 or 20; however, the female disinfecting cover 300 can be larger to accommodate more of the male optical-fiber connector 26 or 30 for disinfection thereof.

The handle 310 can be incorporated into the body 302 or extend therefrom. The handle 310 is configured to enable a person to insert the male optical-fiber connector 26 or 30 into the receptacle 304 or remove the male optical-fiber connector 26 or 30 from the receptacle 304 when holding the female disinfecting cover 300 by the handle 310.

The one-or-more interlocking features (e.g., locking channels, clips, threads, etc.) are configured to interlock with the male optical-fiber connector 26 or 30 and maintain the male optical-fiber connector 26 or 30 in the receptacle 304 when the male optical-fiber connector 26 or 30 is inserted in the female disinfecting cover 300. In addition, with respect to at least E-2000-type male optical-fiber connectors such as the optical-fiber connector 26 or 30, the one-or more interlocking features can be further configured to expose the ferrule 508 and the optical fiber 12 or 20 by moving a cover 512 thereof away from the ferrule 508 and the optical fiber 12 or 20. Again, there are many different male optical-fiber connectors, so the one-or-more interlocking features can vary accordingly.

The body 302, the handle 310, and the one-or-more interlocking features can be integrally molded from a thermoplastic or separately molded and snapped or bonded together. The thermoplastic is selected from acrylonitrile butadiene styrene, polyethylene, polycarbonate, polyimide, high-impact polystyrene, and polypropylene.

The absorbent 506 can be a compressible sponge of polyester, polyurethane, or cellulose. Whether or not the absorbent 506 is a sponge, the absorbent 506 is configured to release a portion of the disinfectant absorbed thereby when compressed into the receptacle 304 by the ferrule 508 of the male optical-fiber connector 26 or 30.

The disinfectant can be an aqueous solution of isopropanol or an iodophor. When the disinfectant is the solution of isopropanol, the solution is at least 70% isopropanol by volume.

The female disinfecting cover 300 can further include a communication module. The communication module is configured to communicate with a medical device including the male optical-fiber connector and indicate to the medical device when the male optical-fiber connector is covered by the female disinfecting cover 300. A cleaning cycle including cleaning or drying is initiated upon the communication module indicating to the medical device the male optical-fiber connector is covered by the female disinfecting cover 300. Actuation of a cleaning action is initiated upon the communication module indicating to the medical device the male optical-fiber connector is covered by the female disinfecting cover 300.

The female disinfecting cover 300 can be integrated into a portal in a procedural barrier for a medical procedure. The portal is configured to enable functional connections between medical devices on opposing sides of the procedural barrier.

Figure 4:
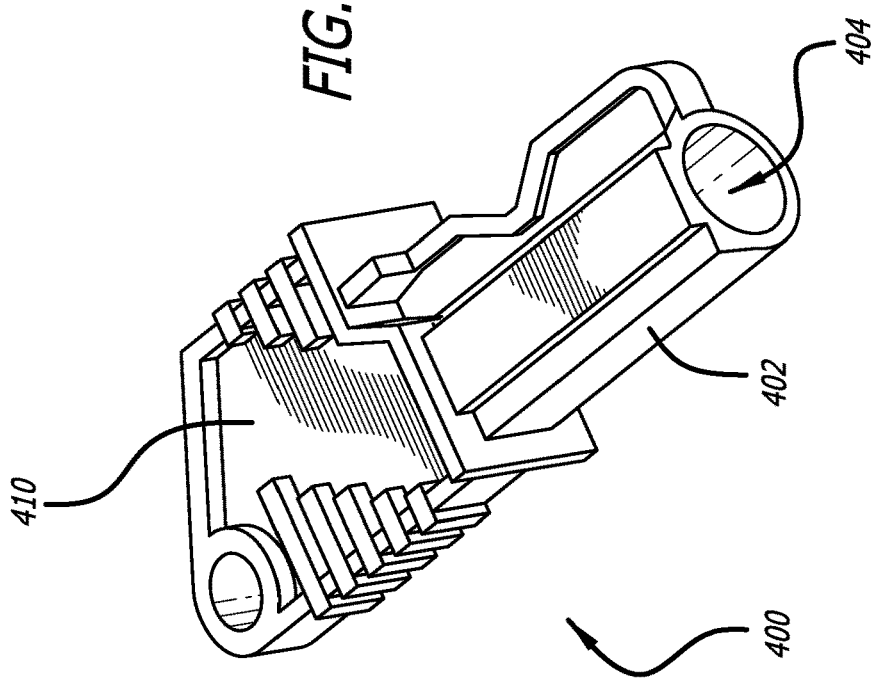
FIG. 4 illustrates a male disinfecting cover for a female optical-fiber connector in accordance with some embodiments.

FIG. 4 illustrates a male disinfecting cover 400 for a female optical-fiber connector in accordance with some embodiments.

As shown, the male disinfecting cover 400 is configured to insert into a receptacle of a female optical-fiber connector such as the female optical-fiber connector 28 or 32 for disinfecting the female optical-fiber connector 28 or 32, as well as protecting the female optical-fiber connector 28 or 32 from dust.

The male disinfecting cover 400 includes a plug 402, a bore 404 of the plug 402, an absorbent disposed in the bore 404, and a disinfectant absorbed by the absorbent. While the absorbent is not shown in FIG. 4, the absorbent is analogous to the absorbent 506 of the female disinfecting cover 300. As shown, the male disinfecting cover 400 can further include a handle 410 opposite the plug 402, as well as one or more interlocking features generally shown. While there are many different female optical-fiber connectors, the female optical-fiber connector 28 or 32 is representative in that it includes a ferrule having an optical fiber disposed therein. The absorbent is configured to contact the ferrule and the optical fiber disposed therein when the male disinfecting cover 400 is inserted into the receptacle of the female optical-fiber connector 28 or 32. Indeed, the bore 404 is configured to accept therein the ferrule of the female optical-fiber connector 28 or 32 to establish such contact. The disinfectant is configured to disinfect at least the ferrule and the optical fiber.

The handle 410 is configured to enable a person to insert the plug 402 into the receptacle of the female optical-fiber connector 28 or 32 or remove the plug 402 from the receptacle of the female optical-fiber connector 28 or 32 by way of the handle 410 when holding the male disinfecting cover 400 by the handle 410.

The one-or-more interlocking features (e.g., locking channels, clips, threads, etc.) are configured to interlock with the female optical-fiber connector 28 or 32 and maintain the plug 402 in the receptacle of the female optical-fiber connector 28 or 32 when the plug 402 of the male disinfecting cover 400 is inserted in the female optical-fiber connector 28 or 32. Again, there are many different female optical-fiber connectors, so the one-or-more interlocking features can vary accordingly.

The plug 402, the handle 410, and the one-or-more interlocking features can be integrally molded from a thermoplastic or separately molded and snapped or bonded together. The thermoplastic is selected from acrylonitrile butadiene styrene, polyethylene, polycarbonate, polyamide, high-impact polystyrene, and polypropylene.

As set forth above, the absorbent can be a compressible sponge of polyester, polyurethane, or cellulose. Whether or not the absorbent is a sponge, the absorbent is configured to release a portion of the disinfectant absorbed thereby when compressed into the bore 404 by the ferrule of the female optical-fiber connector 28 or 32.

The disinfectant can be an aqueous solution of isopropanol or an iodophor. When the disinfectant is the solution of isopropanol, the solution is at least 70% isopropanol by volume.

The male disinfecting cover 400 can further include a communication module. The communication module is configured to communicate with a medical device including the female optical-fiber connector and indicate to the medical device when the female optical-fiber connector is covered by the male disinfecting cover 400. A cleaning cycle including cleaning or drying is initiated upon the communication module indicating to the medical device the female optical-fiber connector is covered by the male disinfecting cover 400. Actuation of a cleaning action is initiated upon the communication module indicating to the medical device the female optical-fiber connector is covered by the male disinfecting cover 400.

The male disinfecting cover 400 can be integrated into a portal in a procedural barrier for a medical procedure. The portal is configured to enable functional connections between medical devices on opposing sides of the procedural barrier.

Methods

Methods include a method for disinfecting optical-fiber connectors such as the male optical-fiber connector 26 or 30 or the female optical-fiber connector 28 or 32. Such a method can include a disconnecting step, a first inserting step, a second inserting step, and a storing step.

The disconnecting step includes disconnecting a male optical-fiber connector from a female optical-fiber connector such as the male optical-fiber connector 26 from the female optical-fiber connector 28 or the male optical-fiber connector 30 from the female optical-fiber connector 32.

The first inserting step includes inserting the male optical-fiber connector 26 or 30 into the female disinfecting cover 300, thereby disinfecting at least the ferrule 508 and the optical fiber 12 or 20 of the male optical-fiber connector 26 or 30. Indeed, the first inserting step includes inserting the male optical-fiber connector 26 or 30 into the receptacle 304 of the female disinfecting cover 300. As set forth above, the receptacle 304 includes the absorbent 506 having the disinfectant absorbed by the absorbent 506. Thus, the first inserting step also includes compressing the absorbent 506 into the receptacle 304, thereby releasing a portion of the disinfectant for the disinfecting of the male optical-fiber connector 26 or 30.

The second inserting step includes inserting the male disinfecting cover 400 into the female optical-fiber connector 28 or 32, thereby disinfecting at least the ferrule and the optical fiber of the female optical-fiber connector 28 or 32. Indeed, the second inserting step includes inserting the plug 402 of the male disinfecting cover 400 into the receptacle of the female optical-fiber connector 28 or 32. As set forth above, the plug 402 includes the bore 404 with the absorbent having the disinfectant absorbed by the absorbent. Thus, the second inserting step includes compressing the absorbent into the bore 404, thereby releasing a portion of the disinfectant for the disinfecting of the female optical-fiber connector 28 or 32.

The storing step includes keeping the male optical-fiber connector 26 or 30 or the female optical-fiber connector 28 or 32 in its respective disinfecting cover until connecting the male optical-fiber connector 26 or 30 or the female optical-fiber connector 28 or 32 to each other or another complementary optical-fiber connector.

As set forth herein, the method mitigates contamination of multiple-use medical devices between uses with different patients.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A disinfecting cover for an optical-fiber connector, comprising:
a body including a receptacle configured to accept the optical-fiber connector therein;
an absorbent disposed in the receptacle configured to contact a ferrule of the optical-fiber connector having an optical fiber disposed therein;
a disinfectant absorbed by the absorbent configured to disinfect at least the ferrule and the optical fiber; and
a communication module configured to:
communicate with a medical device including the optical-fiber connector, and
indicate to the medical device when the optical-fiber connector is covered by the disinfecting cover, wherein a cleaning cycle including cleaning or drying is initiated upon the communication module indicating to the medical device the optical-fiber connector is covered by the disinfecting cover.

2. The disinfecting cover of claim 1, further comprising one or more interlocking features configured to interlock with the optical-fiber connector and maintain the optical-fiber connector in the receptacle of the body when the optical-fiber connector is inserted in the disinfecting cover.

3. The disinfecting cover of claim 1, further comprising a handle incorporated into the body or extending therefrom, the handle configured to enable a person to insert the optical-fiber connector into the receptacle of the body or remove the optical-fiber connector from the receptacle when holding the disinfecting cover by the handle.

4. The disinfecting cover of claim 3, wherein the body and the handle are integrally molded from a thermoplastic selected from acrylonitrile butadiene styrene, polyethylene, polycarbonate, polyamide, high-impact polystyrene, and polypropylene.

5. The disinfecting cover of claim 1, wherein the absorbent is a compressible sponge of polyester, polyurethane, or cellulose.

6. The disinfecting cover of claim 5, wherein the compressible sponge is configured to release a portion of the disinfectant absorbed thereby when compressed into the receptacle of the body by the ferrule of the optical-fiber connector.

7. The disinfecting cover of claim 1, wherein the disinfectant is an aqueous solution of isopropanol.

8. The disinfecting cover of claim 7, wherein the aqueous solution is at least 70% isopropanol by volume.

9. The disinfecting cover of claim 1, wherein actuation of a cleaning action is initiated upon the communication module indicating to the medical device the optical-fiber connector is covered by the disinfecting cover.

10. The disinfecting cover of claim 1, wherein the disinfecting cover is integrated into a portal in a procedural barrier for a medical procedure, the portal configured to enable functional connections between medical devices on opposing sides of the procedural barrier.

11. A method for disinfecting optical-fiber connectors, comprising:
disconnecting a male optical-fiber connector from a female optical-fiber connector;
inserting the male optical-fiber connector into a female disinfecting cover, thereby disinfecting at least a ferrule and an optical fiber of the male optical-fiber connector;
inserting a male disinfecting cover into the female optical-fiber connector, thereby disinfecting at least a ferrule and an optical fiber of the female optical-fiber connector; and
keeping the male optical-fiber connector or the female optical-fiber connector in its respective disinfecting cover until connecting the male optical-fiber connector or the female optical-fiber connector to each other or another complementary optical-fiber connector.

12. The method of claim 11, wherein inserting the male optical-fiber connector into the female disinfecting cover includes inserting the male optical-fiber connector into a receptacle of a body of the female disinfecting cover, the receptacle including an absorbent having a disinfectant absorbed by the absorbent.

13. The method of claim 12, wherein inserting the male optical-fiber connector into the female disinfecting cover includes compressing the absorbent into the receptacle, thereby releasing a portion of the disinfectant for disinfecting the male optical-fiber connector.

14. The method of claim 11, wherein inserting the male disinfecting cover into the female optical-fiber connector includes inserting a plug of the male disinfecting cover into a receptacle of the female optical-fiber connector, the plug including a bore with an absorbent having a disinfectant absorbed by the absorbent.

15. The method of claim 14, wherein inserting the male disinfecting cover into the female optical-fiber connector includes compressing the absorbent into the bore, thereby releasing a portion of the disinfectant for disinfecting the female optical-fiber connector.

16. The method of claim 11, wherein the method mitigates contamination of multiple-use medical devices between uses with different patients.

* * * * *